(12) United States Patent
Chang

(10) Patent No.: US 10,269,105 B2
(45) Date of Patent: Apr. 23, 2019

(54) MASK INSPECTION DEVICE AND METHOD THEREOF

(71) Applicant: ACEMACH CO., LTD, New Taipei (TW)

(72) Inventor: Chih-Chiang Chang, New Taipei (TW)

(73) Assignee: Acemach Co., Ltd., New Taipei (TW)

( * ) Notice: Subject to any disclaimer, the term of this patent is extended or adjusted under 35 U.S.C. 154(b) by 203 days.

(21) Appl. No.: 15/341,806

(22) Filed: Nov. 2, 2016

(65) Prior Publication Data

US 2017/0132778 A1 May 11, 2017

(30) Foreign Application Priority Data

Nov. 6, 2015 (TW) ............................. 104136761 A

(51) Int. Cl.
| | |
|---|---|
| *G01N 21/95* | (2006.01) |
| *G06T 7/00* | (2017.01) |
| *G01B 11/14* | (2006.01) |
| *G01N 21/956* | (2006.01) |
| *H04N 5/225* | (2006.01) |
| *H04N 5/232* | (2006.01) |
| *G06T 7/33* | (2017.01) |

(52) U.S. Cl.
CPC ............ *G06T 7/0004* (2013.01); *G01B 11/14* (2013.01); *G01N 21/956* (2013.01); *G06T 7/337* (2017.01); *H04N 5/2256* (2013.01); *H04N 5/2257* (2013.01); *H04N 5/23203* (2013.01); *G01N 2021/95676* (2013.01); *G01N 2201/025* (2013.01); *G06T 2207/30148* (2013.01)

(58) Field of Classification Search
CPC ................... G01N 2021/95676; G06T 7/0004
USPC .......................................................... 348/92
See application file for complete search history.

(56) References Cited

U.S. PATENT DOCUMENTS 4,347,001 A * 8/1982 Levy ........................ G03F 1/84
356/390

* cited by examiner

*Primary Examiner* — Jeffery A Williams
(74) *Attorney, Agent, or Firm* — Wang Law Firm, Inc.

(57) ABSTRACT

A mask inspection device and method thereof are provided. In the mask inspection device, an image capturing module is controlled to capture an image of the object to be inspected, and when the captured image does not match a predetermined correction image, a horizontal position of the bearing module which holds the object is adjusted; when the captured image matches the predetermined correction image, a light emission element projects a spot light towards the object, and the image capturing module captures an image in a mask region of the object, so as to produce a mask inspection image. The mask inspection information can be obtained from a two-dimensional image of the mask inspection image, and an abnormal image of the mask inspection image is inspected to generate mask abnormal information.

16 Claims, 17 Drawing Sheets

Mask inspection device 1

- The first image capturing module 12
  - Inspection image 120
  - Mask inspection image 121
- Lighting image capturing module 16
  - The first inspection image 160
  - The second inspection image 161
  - Images of through holes 162
- The second image capturing module 19
- The first measuring module 17
  - The first distance inspection signals 170
- Control module 13
  - Correcting inspection signal 130
  - Preset inspection image 131
  - Mask inspection information 132
  - Mask abnormal information 133
  - Measuring signal 134
  - The first inspection signal 135A
  - The second inspection signal 135B
  - The third inspection signal 135C
  - Sidewall inspection signal 136

FIG. 10

After receiving the correcting inspection signal, the control module accordingly controls the first image capturing module to capture the image of the inspected object and accordingly to generate the inspection image — S40

After receiving the inspection image, when the control module determines that the inspection image does not match the predetermined correcting image, the control module controls the rotational shift unit to rotate horizontally to adjust the horizontal position and rotating angle of the bearing module, such that the horizontal position of the inspected object is therefore adjusted. when the control module determines that the inspection image matches the predetermined correcting image, the control module controls the light emission element to project light on the inspected object through the opening, and also controls the first image capturing module to capture the image of the mask region of the inspected object, so as to generate the mask inspection image — S41

After receiving and reading the two-dimensional image of the mask inspecting image, the control module acquires the mask inspection information. The control module also inspects the abnormal image in the mask inspecting image and accordingly generates the mask abnormal information — S42

FIG. 13

```
┌─────────────────────────────────────────────────────────────┐
│ After receiving the first inspection signal, the control module │
│ accordingly drives the lifting unit to move in the first direction, such that │──S43
│ the lighting image capturing module moves closer to the inspected object │
└─────────────────────────────────────────────────────────────┘
                              ↓
┌─────────────────────────────────────────────────────────────┐
│ The control module controls the rotational shift unit to drive the light │
│ emission element to project the first spot light on the inspected object │──S44
│ through the opening and controls the rotational shift unit to move in the │
│ second or the third direction, so as to carry the bearing module to move │
└─────────────────────────────────────────────────────────────┘
                              ↓
┌─────────────────────────────────────────────────────────────┐
│ The control module controls the lighting image capturing module to │
│ capture the images of the first regions of the inspected object and │──S45
│ generates the first inspection images │
└─────────────────────────────────────────────────────────────┘
                              ↓
┌─────────────────────────────────────────────────────────────┐
│ After receiving the second inspection signal, the control module │
│ accordingly drives the lighting image capturing module to project the │
│ second spot light on the inspected object and controls the rotational │──S46
│ shift unit to move in the second or the third direction, so as to carry the │
│ bearing module to move │
└─────────────────────────────────────────────────────────────┘
                              ↓
┌─────────────────────────────────────────────────────────────┐
│ The control module controls the lighting image capturing module to │
│ capture images of the second regions of the inspected object and │──S47
│ generates the second inspection images │
└─────────────────────────────────────────────────────────────┘
                              ↓
┌─────────────────────────────────────────────────────────────┐
│ After receiving the third inspection signal, the control module drives the │
│ lifting unit to move in the first direction, such that the lighting image │──S48
│ capturing module moves closer to the inspected object │
└─────────────────────────────────────────────────────────────┘
                              ↓
┌─────────────────────────────────────────────────────────────┐
│ The control module controls the first lighting module to move towards │
│ the bearing module, such that the condenser unit moves to the position │
│ between the rotational shift unit and the bearing module and │──S49
│ correspondingly facing the lighting image capturing module │
└─────────────────────────────────────────────────────────────┘
                              ↓
┌─────────────────────────────────────────────────────────────┐
│ The control module controls the rotational shift unit to carry the bearing │
│ module to move and controls the condenser unit to project the focused │──S50
│ light on one of the through holes of the inspected object through the │
│ opening │
└─────────────────────────────────────────────────────────────┘
                              ↓
┌─────────────────────────────────────────────────────────────┐
│ The control module controls the lighting image capturing module to │──S51
│ sequentially capture and generate the images of the through holes │
└─────────────────────────────────────────────────────────────┘
```

FIG. 14

| After receiving the measuring signal, the control module controls the distance measuring module to project distance measuring light on the inspected object | — S450 |

↓

| The distance measuring module receives distance measuring light reflected from the inspected object to generate the inspection distance signal | — S451 |

↓

| After receiving the first inspection signal and the inspection distance signal, the control module drives the lifting unit to move in the first direction, such that the lighting image capturing module is spaced apart from the inspected object by the predetermined working distance | — S452 |

↓

| The control module controls the rotational shift unit to drive the light emission element to project the first spot light on the inspected object through the opening and controls the rotational shift unit to carry the bearing module to move | — S453 |

↓

| The control module controls the lighting image capturing module to capture the images of the plurality of first regions of the inspected object and to generate the first inspection images | — S454 |

FIG. 15

After receiving the sidewall inspection signal, the control module controls the rotational shift unit to carry the bearing module to move to the image capturing region of the second image capturing module — S52

The control module controls the first measuring module to sequentially and respectively project first measuring light on the inner wall surfaces of the frame on one surface of the inspected object and to receive the first measuring light reflected from each inner wall surface to respectively generate the first distance inspection signals — S53

Respectively based on the plurality of first distance inspection signals of inner wall surfaces, the control module controls the rotational shift unit to sequentially carry the bearing module to move in the second or the third direction or to rotate horizontally, so as to adjust the distance between each inner wall surface and the second image capturing module to the predetermined image capturing distance. The control module also controls the second lighting module to project the third light on each inner wall surface and controls the second image capturing module to sequentially capture the image of each inner wall surface, so as to generate the plurality of inner wall inspection images — S54

FIG. 16

After receiving the flatness inspection signal, the control module accordingly controls the rotational shift unit to carry the bearing module to move to the image capturing region of the third image capturing module — S55

The control module controls the second measuring module to sequentially and respectively project the second measuring light on the surface regions of the film body of the inspected object and to receive the second measuring light reflected from the inspected object so as to generate the plurality of the second distance inspection signals, and the control module also controls the light emission element to project first spot light on the inspected object through the opening and controls the third image capturing module to capture images of the inspected object so as to generate the plurality of inspection images of the inspected object — S56

The control module controls the light emission element to project the first spot light on the inspected object through the opening and sequentially controls the supporting unit to move based on the plurality of second distance inspection signals so as to adjust the distance between the third image capturing module and each surface region to the predetermined image capturing distance — S57

The control module controls the third image capturing module to respectively capture the image of each surface region so as to generate the inspection images of the inspected object — S58

The control module generates the flatness information of the inspected object based on the second distance inspection signals — S59

The white-light interference image capturing module receives the inspection images of the inspected object and generates the anomaly size information and anomaly location information by using a white light contrast interference manner — S60

FIG. 17

MASK INSPECTION DEVICE AND METHOD THEREOF

CROSS-REFERENCE TO RELATED APPLICATION

This application claims priority from Taiwan Patent Application No. 104136761, filed on Nov. 6, 2015 in the Taiwan Intellectual Property Office, the content of which is hereby incorporated by reference in its entirety for all purposes.

BACKGROUND OF THE INVENTION

1. Field of the Invention

The present invention relates to an inspection device and an inspection method, and particularly relates to a mask inspection device that inspects defects on a mask and the method thereof.

2. Description of the Related Art

In the current technology of semiconductor fabrication, circuit patterns of a semiconductor device are formed on the surface of a wafer by printing them through a mask or a reticle.

As the dimension of the semiconductor device shrinks, defects of the mask can greatly impact the quality, such as pattern distortion or malformation, of circuit patterns on a silicon wafer during manufacturing a semiconductor device. The most commonly known cause of the defect is particles that attach on the surface of a mask.

Therefore, how to inspect a mask and identify whether if there are particles attached on its surface is a considerably urgent issue in the associated industry to be dealt with.

The inventors of the present invention design a mask inspection device to solve the current technical issues and to improve the industrial practical applicability.

SUMMARY OF THE INVENTION

In view of the issues of the aforementioned conventional technique, the purpose of the present invention is to provide a mask inspection device to solve the current technical issues.

To achieve the purpose, the present invention provides a mask inspection device, which includes a device main body, a bearing module, a first image capturing module, and a control module. The device main body includes a rotational shift unit movably disposed with a surface thereof, and a light emission element disposed on a surface of the rotational shift unit. The bearing module is suspended on a surface of the rotational shift unit, and an inspected object is movably carried on the surface of the bearing module opposing to the surface facing the rotational shift unit. The main body of the bearing module has an opening. The first image capturing module is suspended on the surface of the device main body. The control module is electrically engaged with the rotational shift unit and the first image capturing module. The control module receives a correcting inspection signal and accordingly controls the first image capturing module to capture the image of the inspected object so as to generate an inspection image. After the control module receives the inspection image, when the control module determines that the inspection image does not match a predetermined correction image, the control module controls the rotational shift unit to rotate horizontally so as to adjust a horizontal position and a rotational angle of the bearing module, such that the horizontal position of the inspected object is therefore adjusted; when the control module determines that the inspection image matches the predetermined correction image, the control module controls the light emission element to project a first spot light on the inspected object and controls the first image capturing module to capture an image of a mask region of the inspected object to generate a mask inspection image, and the control module receives and reads a two-dimensional image of the mask inspection image to acquire mask inspection information and inspects an abnormal image contained in the mask inspection image to generate mask abnormal information.

Preferably, a lifting unit is disposed on the surface of the device main body, and the mask inspection device preferably includes a lighting image capturing module disposed on the lifting unit. The control module receives the first inspection signal and accordingly drives the lifting unit to move in a first direction, such that the lighting image capturing module moves closer to the inspected object; the control module controls the rotational shift unit to drive the light emission element to project the first spot light on the inspected object through the opening and controls the rotational shift unit to move in a second direction or in a third direction in a step manner so as to drive movement of the bearing module; the control module also controls the lighting image capturing module to capture the images of a plurality of first regions of the inspected object so as to generate a plurality of first inspection images.

Preferably, the control module receives the second inspection signal and accordingly drives the lighting image capturing module to project a second spot light on the inspected object, and the control module controls the rotational shift unit to move in the second direction or the third direction in a step manner to drive the movement of the bearing module, and the control module controls the lighting image capturing module to capture the images of a plurality of second regions of the inspected object, so as to generate a plurality of second inspection images.

Preferably, the mask inspection device further comprises a distance measuring module electrically connected to the control module and disposed on the lifting unit, and the control module receives a measuring signal and accordingly controls the distance measuring module to project at least one distance measuring light on the inspected object, and the distance measuring module receives at least one distance measuring light reflected from the inspected object to generate an inspection distance signal, and the control module receives the first inspection signal and the inspection distance signal and accordingly drives the lifting unit to move in the first direction, such that the distance between the lighting image capturing module and the inspected object is a predetermined working distance, and the control module controls the rotational shift unit to drive the light emission element to project the first spot light on the inspected object through the opening and controls the rotational shift unit to carry the bearing module to move, and the control module controls the lighting image capturing module to capture the images of the plurality of the first regions of the inspected object so as to generate the plurality of the first inspection images.

Preferably, the mask inspection device further comprises the first lighting module which is movably disposed on the device main body by an end thereof, and a condenser unit is disposed on the other end of the first lighting module. The control module receives the third inspection signal and accordingly drives the lifting unit to move in the first direction so as to move the lighting image capturing module closer to the inspected object and controls the first lighting module to move towards the bearing module, such that the condenser unit is moved to the position between the rotational shift unit and the bearing module and correspondingly facing the lighting image capturing module, and the control module controls the rotational shift unit to drive the movement of the bearing module and controls the condenser unit to project a focused light on one of a plurality of through holes of the inspected object through the opening, such that the lighting image capturing module sequentially captures the images of the plurality of through holes and generates images of the plurality of through holes.

Preferably, a supporting unit is disposed on the surface of the device main body, and the mask inspection device further includes a second image capturing module, a first measuring module, and a second lighting module. The second image capturing module is disposed on the supporting unit to capture the image of the inspected object. The first measuring module is disposed on one side of the second image capturing module, and the second lighting module is disposed on the other side of the second image capturing module. The control module receives a sidewall inspection signal and accordingly controls the rotational shift unit to carry the bearing module to move to the image capturing region of the second image capturing module, and the control module controls the rotational shift unit to sequentially rotate the bearing module and controls the first measuring module to sequentially and respectively project the first measuring lights on a plurality of inner wall surfaces of a frame on a surface of the inspected object, and the first measuring module receives the plurality of first measuring lights respectively reflected from inner wall surfaces and respectively generates the first distance inspection signals. The control module drives the rotational shift unit to carry the bearing module to move in the second direction or the third direction or to rotate horizontally based on the plurality of first distance inspection signals of the inner wall surface so as to adjust the distance between each inner wall surface and the second image capturing module to a predetermined image capturing distance and controls the second lighting module to project a third spot light on each inner wall surface and controls the second image capturing module to sequentially capture image of each of the inner wall surfaces, so as to generate a plurality of inner wall inspection images.

Preferably, a supporting unit is disposed on the surface of the device main body, and the mask inspection device further includes the third image capturing module and the second measuring module. The third image capturing module is disposed on the supporting unit to capture the image of the inspected object. The second measuring module is disposed on one side of the third image capturing module. The control module receives a flatness inspection signal and accordingly controls the rotational shift unit to carry the bearing module to move to an image capturing region of the third image capturing module, and the control module controls the second measuring module to sequentially project second measuring light on a plurality of surface regions of a film body of the inspected object and to receive the second measuring light reflected from the plurality of surface regions so as to generate a plurality of second distance inspection signals, and the control module controls the light emission element to project the first spot light on the inspected object through the opening, and sequentially controls the supporting unit to move based on the plurality of second distance inspection signals so as to adjust the distance between the third image capturing module and each surface region to a predetermined image capturing distance. The control module respectively controls the third image capturing module to capture the image of each surface region to generate a plurality of inspection images of the inspected object, and the control module generates flatness information of the inspected object based on the plurality of the second distance inspection signals.

Preferably, the mask inspection device further comprises a white-light interference image capturing module electrically connected to the control module. The white-light interference image capturing module receives the plurality of inspection images of the inspected object to generate anomaly size information and anomaly location information by using a white light contrast interference manner.

To achieve the purpose, the present invention also provides a mask inspection method comprising the following steps.

After receiving a correcting inspection signal, a control module accordingly controls a first image capturing module to capture an image of an inspected object and accordingly to generate an inspection image.

After receiving the inspection image, when the control module determines that the inspection image does not match the predetermined correction image, the control module controls a rotational shift unit to rotate horizontally so as to adjust a horizontal position and a rotating angle of a bearing module, such that a horizontal position of the inspected object is adjusted; when the control module determines that the inspection image matches the predetermined correction image, the control module controls a light emission element to project light on the inspected object through an opening and also controls the first image capturing module to capture the image of a mask region of the inspected object and to generate a mask inspection image.

After receiving and reading a two-dimensional image of the mask inspection image, the control module acquires mask inspection information, and the control module also inspects an abnormal image in the mask inspection image and accordingly generates mask abnormal information.

Preferably, the mask inspection method further comprises the following steps.

After receiving a first inspection signal, the control module accordingly drives a lifting unit to move in a first direction, such that a lighting image capturing module moves closer to the inspected object.

The control module controls the rotational shift unit to drive the light emission element to project the first spot light on the inspected object through the opening and controls the rotational shift unit to move in the second or the third direction in a step manner, so as to drive movement of the bearing module.

The control module controls the lighting image capturing module to capture the images of a plurality of first regions of the inspected object and to generate a plurality of first inspection images.

Preferably, the mask inspection method further comprises the following steps.

After receiving the second inspection signal, the control module accordingly drives the lighting image capturing module to project the second spot light on the inspected object and controls the rotational shift unit to step to move in the second or the third direction so as to drive movement of the bearing module.

The control module controls the lighting image capturing module to capture the images of a plurality of second regions of the inspected object and to generate a plurality of second inspection images.

Preferably, the mask inspection method further comprises the following steps.

After receiving a measuring signal, the control module accordingly controls a distance measuring module to project at least one distance measuring light on the inspected object.

The distance measuring module receives at least one distance measuring light reflected from the inspected object to generate an inspection distance signal.

After receiving the first inspection signal and the inspection distance signal, the control module accordingly drives the lifting unit to move in the first direction, such that the lighting image capturing module is at the predetermined working distance away from the inspected object.

The control module controls the rotational shift unit to drive the light emission element to project the first spot light on the inspected object through the opening and controls the rotational shift unit to carry the bearing module to move.

The control module controls the lighting image capturing module to capture the images of a plurality of first regions of the inspected object and to generate a plurality of first inspection images.

Preferably, the mask inspection method further comprises the following steps.

After receiving the third inspection signal, the control module accordingly drives the lifting unit to move in the first direction, such that the lighting image capturing module moves closer to the inspected object.

The control module controls the first lighting module to move towards the bearing module, such that a condenser unit moves to the position between the rotational shift unit and the bearing module and correspondingly facing the lighting image capturing module.

The control module controls the rotational shift unit to carry the bearing module to move and controls the condenser unit to project a focused light on one of a plurality of through holes of the inspected object through the opening.

The control module controls the lighting image capturing module to sequentially capture and generate the images of the plurality of through holes.

Preferably, the mask inspection method further comprises the following steps.

After receiving the sidewall inspection signal, the control module accordingly controls the rotational shift unit to carry the bearing module to move to the image capturing region of the second image capturing module.

The control module controls the first measuring module to sequentially and respectively project the plurality of first measuring lights on the plurality of inner wall surfaces of the frame on one surface of the inspected object and to receive the plurality of first measuring lights reflected from each inner wall surface so as to respectively generate the first distance inspection signals.

Respectively based on the plurality of first distance inspection signals of the inner wall surfaces, the control module controls the rotational shift unit to sequentially carry the bearing module to move in the second or the third direction or to rotate horizontally so as to adjust the distance between each inner wall surface and the second image capturing module to the predetermined image capturing distance, and the control module also controls the second lighting module to project the third spot light on each inner wall surface and controls the second image capturing module to sequentially capture the image of each inner wall surface so as to generate a plurality of inner wall inspection images.

Preferably, the mask inspection method further comprises the following steps.

After receiving the flatness inspection signal, the control module accordingly controls the rotational shift unit to carry the bearing module to move to an image capturing region of the third image capturing module.

The control module controls the second measuring module to sequentially and respectively project the second measuring light on a plurality of surface regions of a film body of the inspected object and to receive the second measuring light reflected from the inspected object so as to generate a plurality of second distance inspection signals.

The control module controls the light emission element to project the first spot light on the inspected object through the opening and sequentially controls a supporting unit to move based on the plurality of second distance inspection signals, so as to adjust the distance between the third image capturing module and each surface region to the predetermined image capturing distance.

The control module controls the third image capturing module to respectively capture the image of each surface region so as to generate a plurality of inspection images of the inspected object.

The control module generates flatness information of the inspected object based on the plurality of the second distance inspection signals.

Preferably, the mask inspection method further comprises the following steps.

A white-light interference image capturing module is used to receive the plurality of inspection images of the inspected object and generate anomaly size information and anomaly location information by using the white light contrast interference manner.

As aforementioned, the mask inspection device and the method thereof have one or more following advantages:

1. The mask inspection device and the method thereof of the present invention have the advantage of adjusting a mask to the correct position determined by the control module. It is achieved by comparing the inspection image captured by the image capturing module with the predetermined correction image.

2. The mask inspection device and the method thereof of the present invention have the advantage of improving the accuracy of the anomaly inspection on an inspected object. The bearing module is driven by the device main body to move in the step manner and the image capturing module is controlled to capture images of the plurality of regions of the inspected object, so as to acquire high quality and clear micro-images for an operator to determine if there is anomaly on the inspected object.

3. The mask inspection device and the method thereof of the present invention have the advantage of inspection with precision and improvement in the yield of lithography. The measuring modules are used to measure the inspected regions and the rotational shift unit is controlled to move before the image capturing module capturing the inspection images of the inspection regions.

BRIEF DESCRIPTION OF THE DRAWINGS

FIG. 10 is a block diagram showing the third embodiment of the mask inspection device of the present invention.

FIG. 13 is a first flow chart of the mask inspection method of the present invention.

FIG. 14 is a second flow chart of the mask inspection method of the present invention.

FIG. 15 is a third flow chart of the mask inspection method of the present invention.

FIG. 16 is a fourth flow chart of the mask inspection method of the present invention.

FIG. 17 is a fifth flow chart of the mask inspection method of the present invention.

DESCRIPTION OF THE PREFERRED EMBODIMENTS

For better understanding the features, the content, the advantages and the effects, the present invention will be presented hereinafter through preferable embodiments accompanying with corresponding figures. Since being only for the illustrative and auxiliary purposes, the figures are not necessarily implying the actual ratio or precise configuration of the products of the present invention. Therefore, the claims of the present invention that are actually applied, should not be limited by the figures' ratio and configuration.

Figure 1:
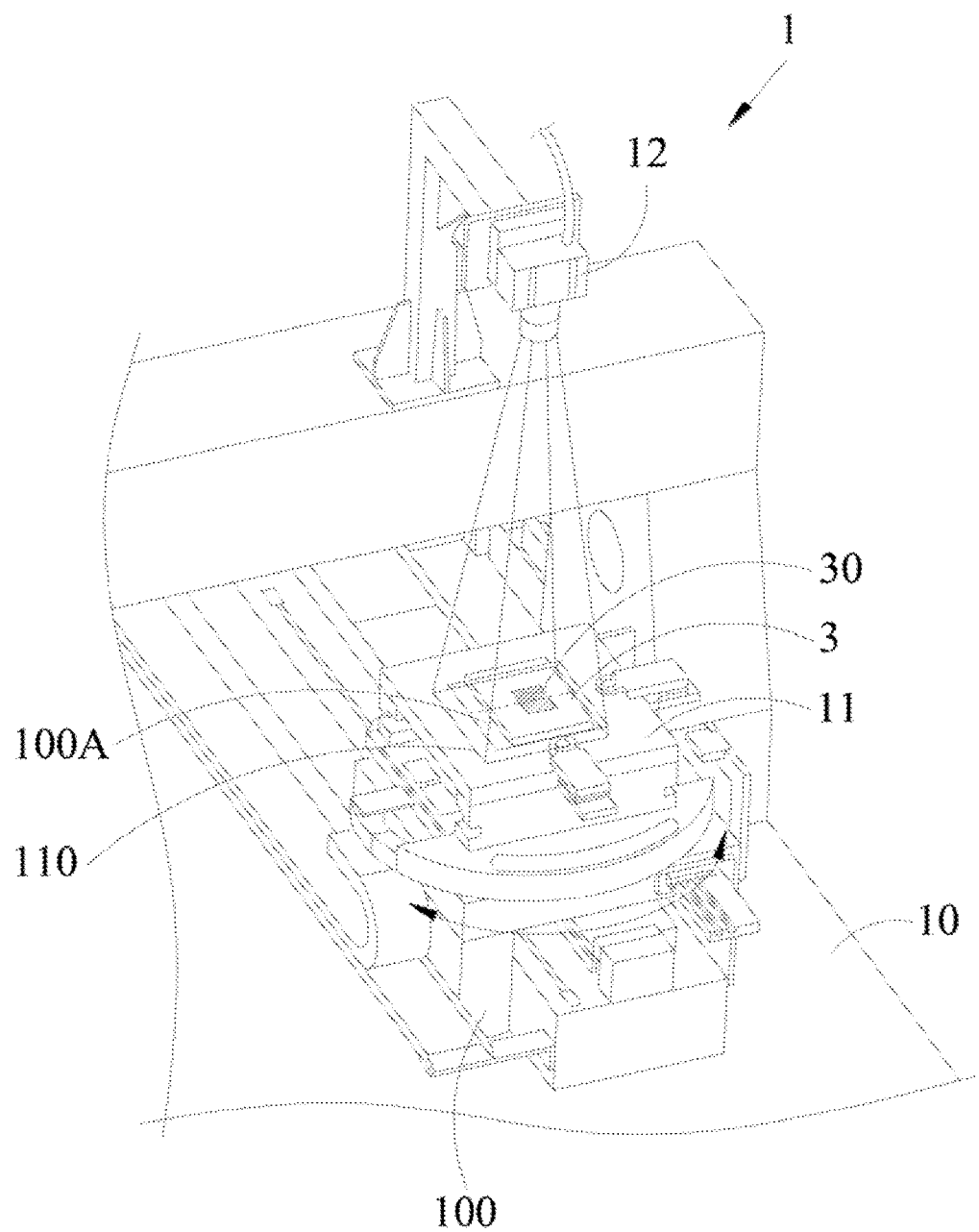
FIG. 1 is a structural diagram showing the first embodiment of the mask inspection device of the present invention.
Figure 2:
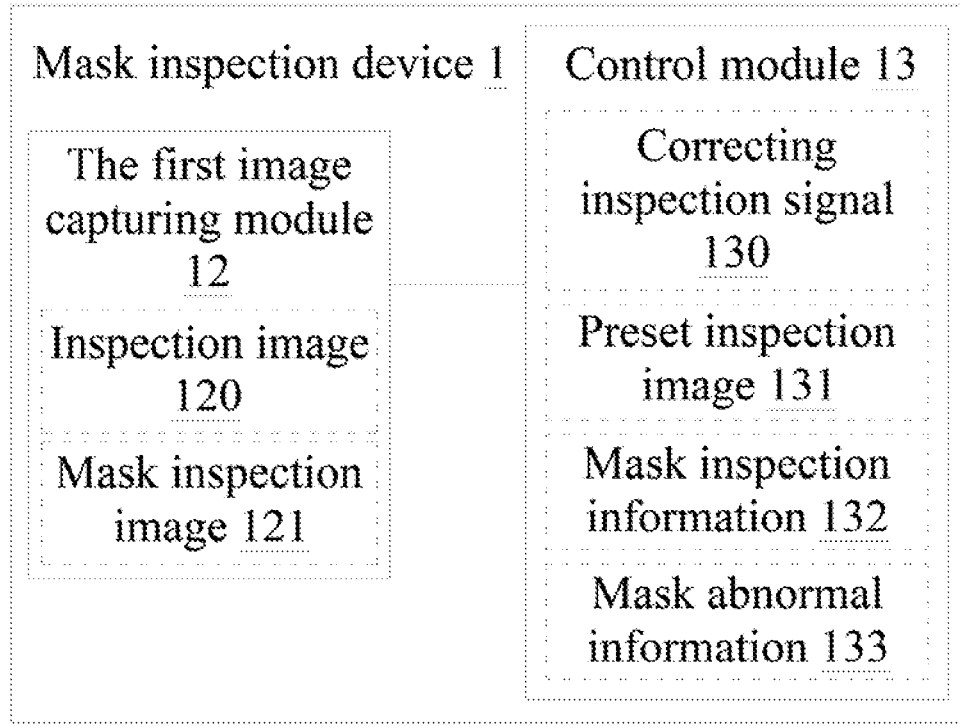
FIG. 2 is a block diagram showing the first embodiment of the mask inspection device of the present invention.
Figure 3:
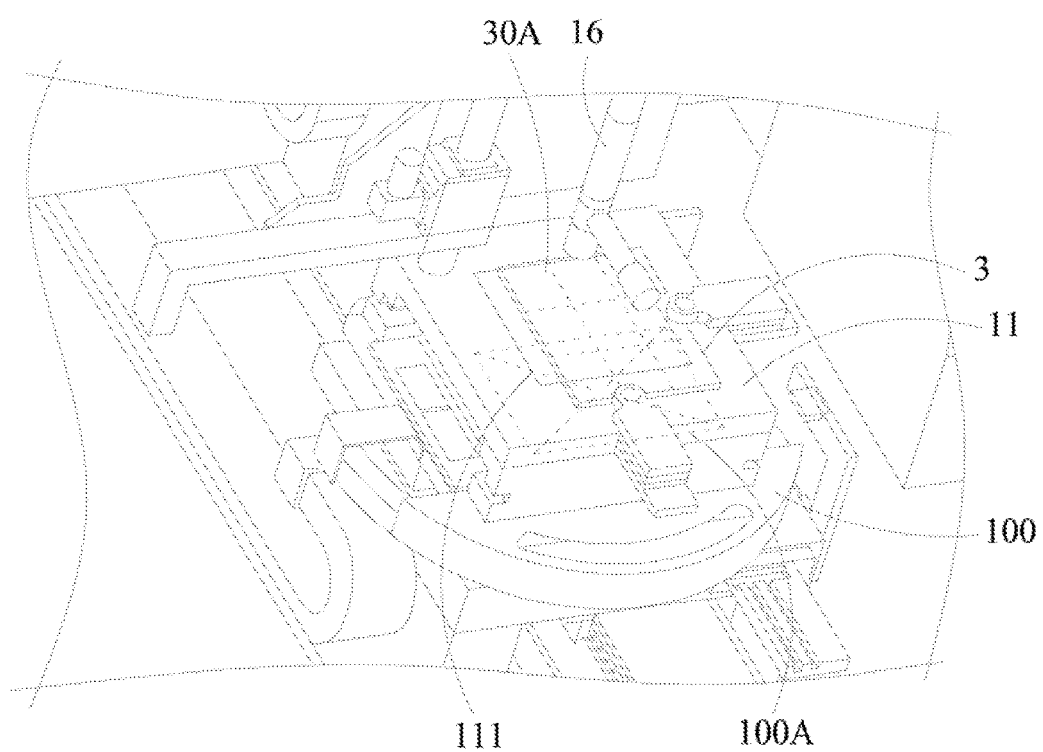
FIG. 3 is a first schematic diagram showing a second embodiment of the mask inspection device of the present invention.
Figure 4:
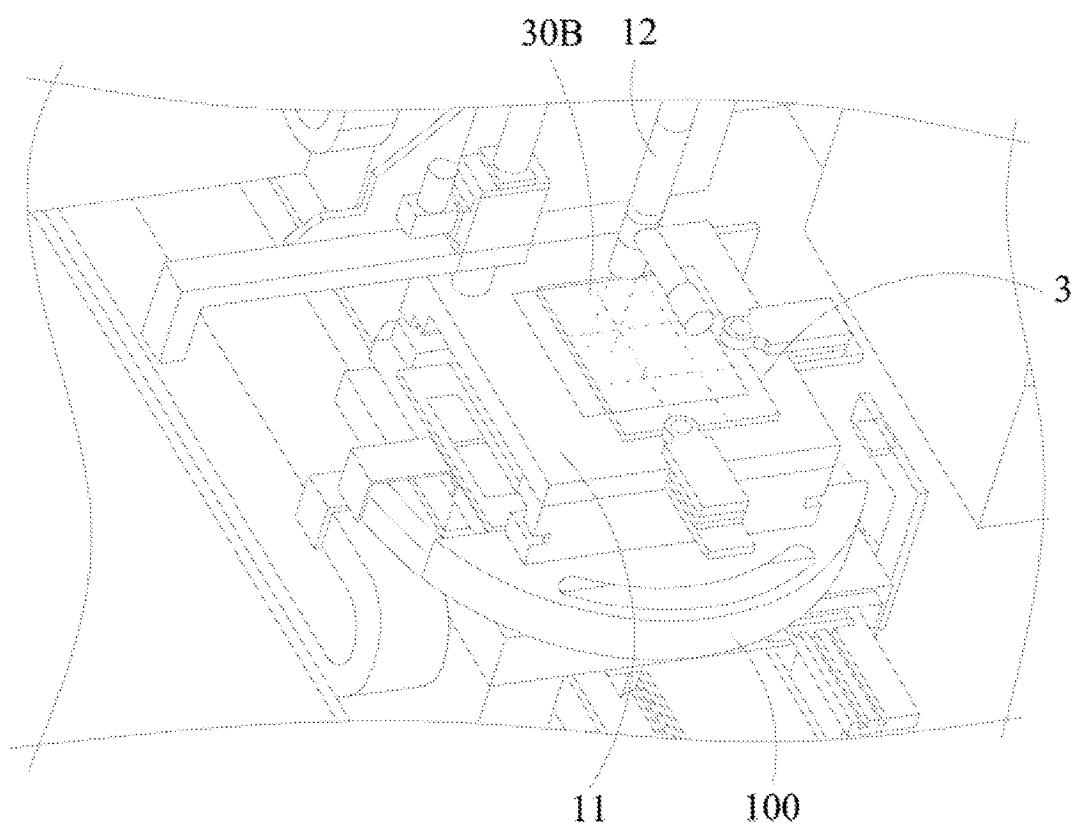
FIG. 4 is a second schematic diagram showing the second embodiment of the mask inspection device of the present invention.
Figure 5:
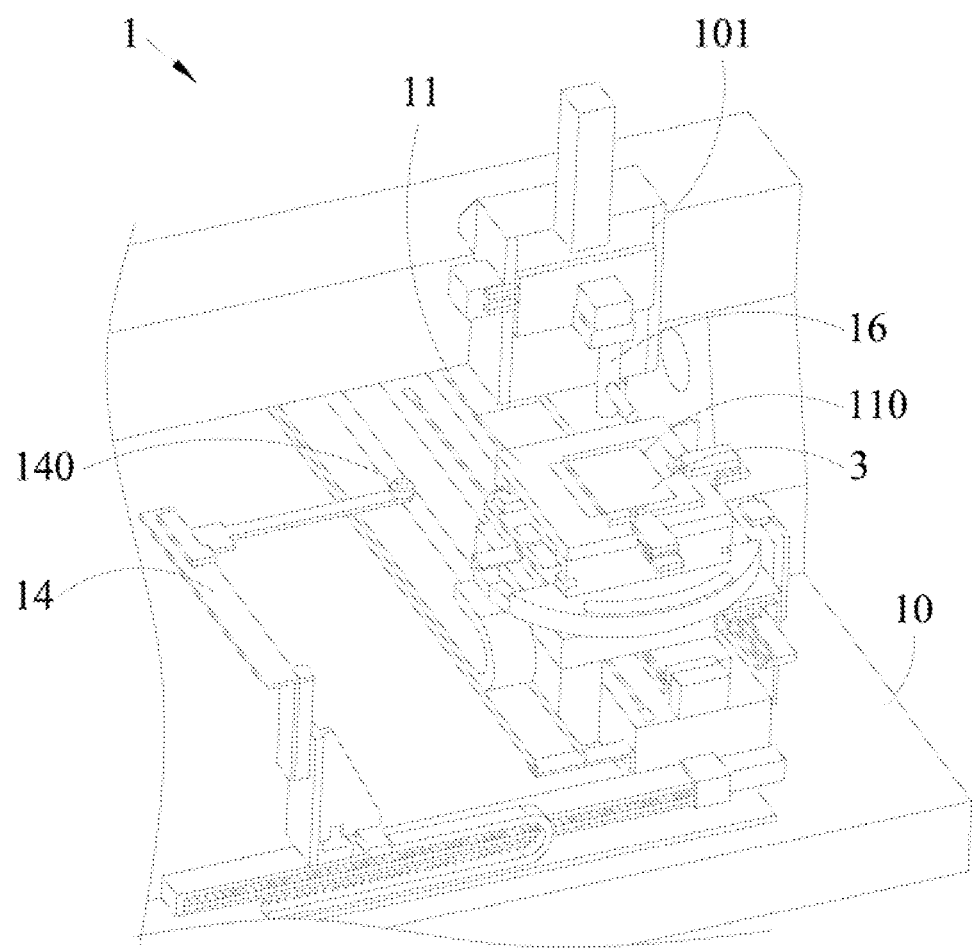
FIG. 5 is a third schematic diagram showing the second embodiment of the mask inspection device of the present invention.
Figure 6:
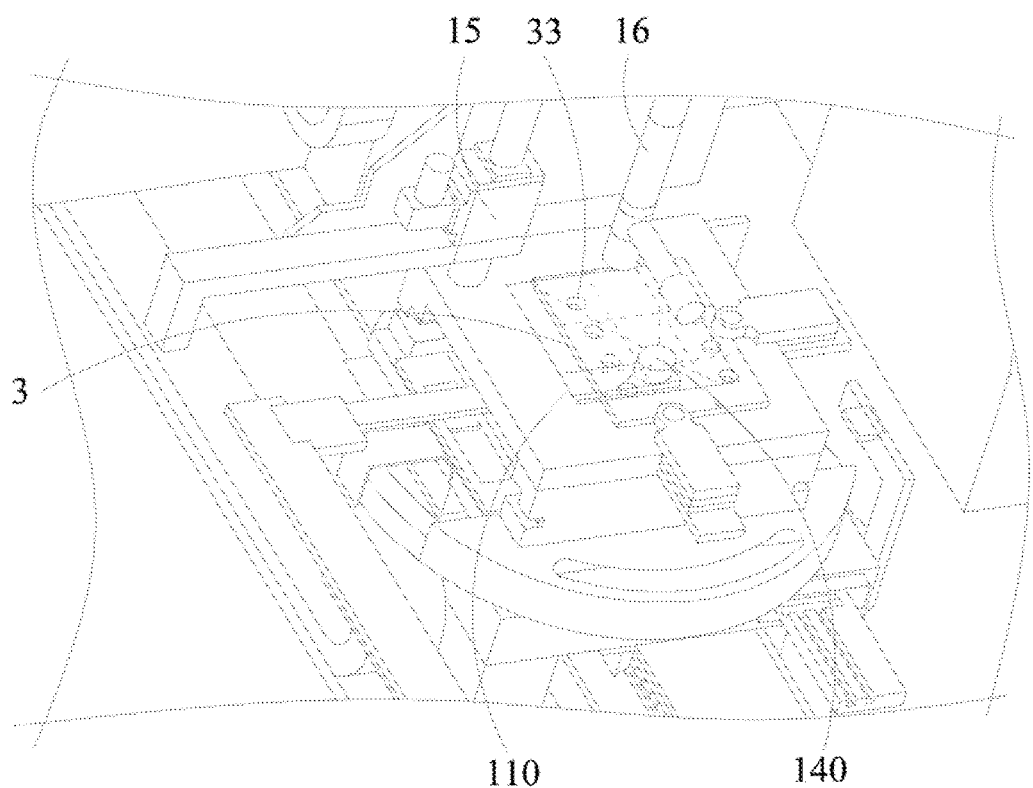
FIG. 6 is a fourth schematic diagram showing the second embodiment of the mask inspection device of the present invention.
Figure 7:
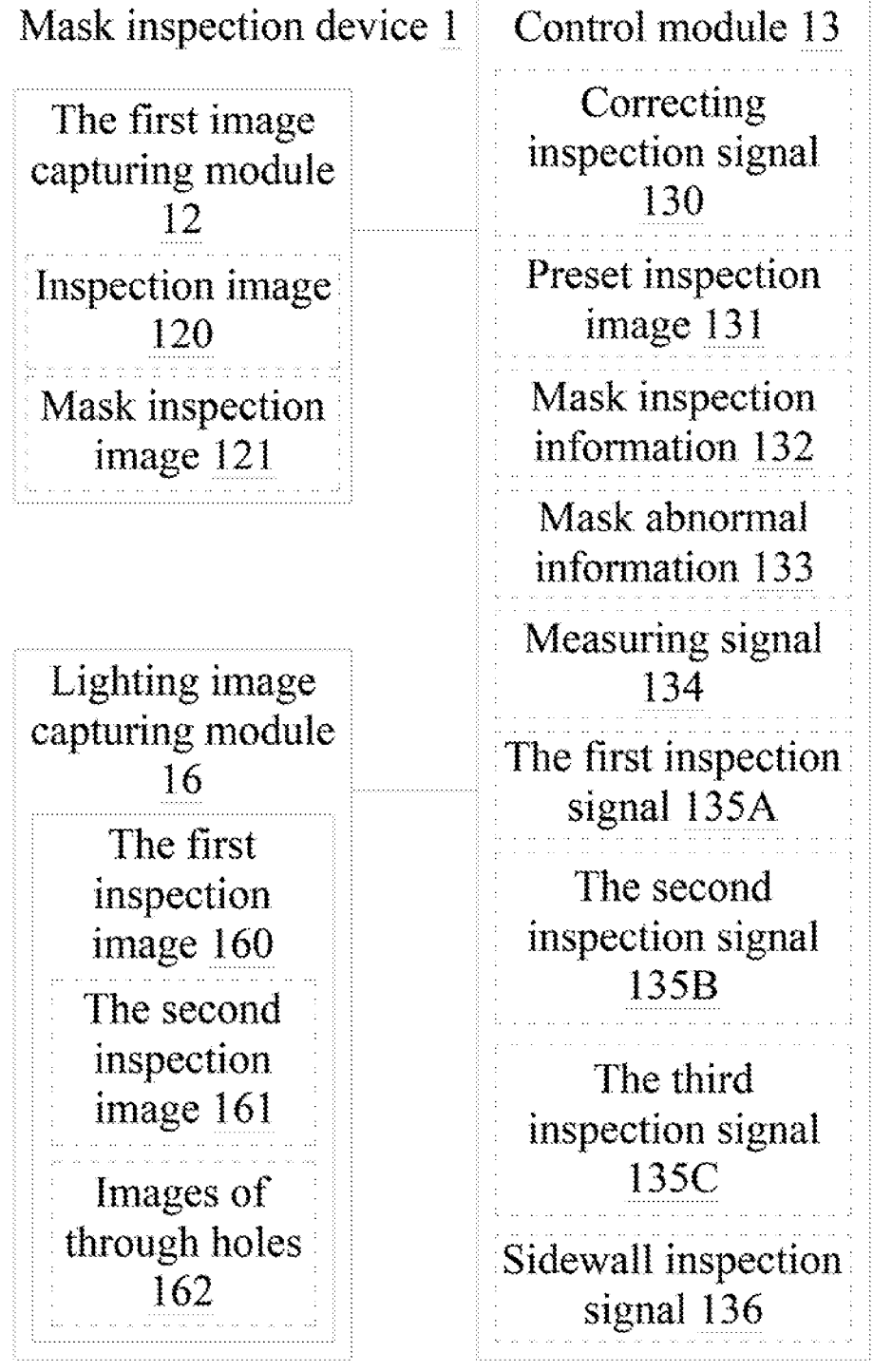
FIG. 7 is a block diagram showing the second embodiment of the mask inspection device of the present invention.

The embodiments of the mask inspection device and the method thereof of the present invention will be described referring to the corresponding figures. For better understanding, the same elements will be designated by the same reference numerals through embodiments Refer to FIGS. 1 and 2. The mask inspection device 1 includes a device main body 10, a bearing module 11, a first image capturing module 12, and a control module 13. A rotational shift unit 100 is movably disposed on a surface of the device main body 10, and a light emission element 100A is disposed one surface of the device main body 10. The bearing module 11 is suspended on a surface of the rotational shift unit 100, and an inspected object 3 is movably carried on the surface of the bearing module 11 opposing to the surface facing the rotational shift unit 100. The bearing module 11 has an opening 110. The first image capturing module 12 is suspended on the same surface of the device main body. The control module 13 is electrically engaged with the rotational shift unit 100 and the first image capturing module 11. The control module 13 receives the correcting inspection signal 130, according to which the control module 13 controls the first image capturing module 12 to take an image of the inspected object 3, and accordingly generates the inspection image 120. When receiving the image of the inspected object 3 and determining that the inspection image 120 does not match the preset inspection image 131, the control module 13 controls the rotational shift unit 100 to rotate horizontally to adjust a horizontal position and a rotational angle of the bearing module 11, such that a horizontal position of the inspected object 3 is accordingly adjusted. On the other hand, when determining that the inspection image 120 matches the preset inspection image 131, the control module 13 controls the light emission element 100A to project the first spot light on the inspected object 3 through the opening 110 and controls the first image capturing module 12 to capture the image of the mask region 30 of the inspected object 3 and to generate a mask inspection image 121. The control module 13 then receives and reads the two-dimensional image of the mask inspection image 121 to acquire mask inspection information 132 and also inspects the abnormal images in the mask inspection image 121 to generate mask abnormal information 133.

Specifically, the mask inspection device 1 of the present invention provides the function of adjusting a mask to the correct position. The function is accomplished by taking an inspection image 129 by the first image capturing module 12, and then comparing the inspection image 129 with the preset inspection image 131 by the control module 13 to determine if the position is correct. In this case, the mask inspection device 1 of the present invention includes the device main body 10, the bearing module 11, the first capturing module 12, and the control module 13. A rotational shift unit 100 is movably disposed on one surface of the device main body 10, and includes the functions to provide horizontal adjustability of forward and backward and of right-to-left and to provide rotation adjustability on the horizontal surface. A surface of the rotational shift unit 100 is disposed with the light emission element 100A. The bearing module 11 is suspended on the surface of the rotational shift unit 100, and the inspected object 3 is movably carried on the surface of the bearing module 11 opposing to the surface facing the rotational shift unit 100. The inspected object 3 can include a substrate, such as a quartz plate, a frame, and a thin film. The substrate includes a mask, and the frame is disposed on the substrate and covers the thin film. The first capturing module 12, which can capture an image of the inspected object 3, is suspended on the same surface of the device main body. The control module 13 is electrically engaged to the rotational shift unit 100 and the first capturing module 11.

During the inspection performed on the inspected object 3 by the mask inspection device 1, the control module 13 receives the correcting inspection signal 130, which is provided by an operator through an input device (not shown in the figures), such as a keyboard, a touch-pad, etc. According to the correcting inspection signal 130, the control module 13 controls the first capturing module 12 to capture an image of the inspected object 3 and generate the inspection image 120, which is then sent back to the control module 13. After receiving the inspection image 120, the control module 13 performs the comparison between the inspection image 120 with the preset inspection image 131. When the inspection image 120 does not match the preset inspection image 131, the control module 13 controls the rotational shift unit 100 to rotate horizontally to adjust the horizontal position and the rotational angle of the bearing module 11. A range of the angle is from 0 to 360 degrees. After the bearing module 11 is adjusted, the control module 13 once again controls the first capturing module 12 to capture the other image of the inspected object 3 to generate the other inspection image and determines whether if this inspection image matches the preset inspection image 131. If not, the rotational shift unit 100 is again driven to rotate horizontally to adjust the horizontal position and the rotational angle of the bearing module 11. The procedure is continuously performed until the inspection image matches the preset inspection image 131.

After determining that the inspection image 120 matches the preset inspection image 131, the control module 13 controls the light emission element 100A to project the first spot light on the inspected object 3 through the opening 110 and controls the first image capturing module 12 to capture the image of the mask region 30 of the inspected object 3 and to generate a mask inspection image 121. The control module 13 then reads the two-dimensional image, which can be a barcode including information such as the name, the type, the size of the mask, on the mask inspection image 121 to acquire the mask inspection information 132 of the inspected object 3, and the control module 13 also inspects the abnormal images in the mask inspection image 121, such as particles, to generate mask abnormal information 133, so as to provide operators the information to check if the inspected object 3 is abnormal.

The control module 13 can further include a storage device such as memory or hard disk, to store the aforementioned various kinds of images and information.

It should be noted that a metal mesh (not shown in the figures) can be included between the rotational shift unit 100 and the light emission element 100A in the mask inspection device 1. Preferably, the metal mesh is formed of copper, so that the metal mesh of the mask inspection device 1 can isolate the light emission element 100A from the electromagnetic influence of the rotational shift unit 100. Therefore, the luminance or brightness of the light emission element 100A is prevented from being affected.

Referring to FIGS. 3-7, these figures are the first schematic diagram, the second schematic diagram, the third schematic diagram, the fourth schematic diagram and the block diagram respectively showing the mask inspection device of a second embodiment of the present invention. Also refer to FIGS. 1 and 2. As shown in the figures, the same elements act similarly as those in the first embodiment, so their descriptions are therefore omitted. In this embodiment, a lifting unit 101 is disposed on the surface of the device main body 10. The mask inspection device 1 preferably includes a lighting image capturing module 16, which is disposed on the lifting unit 101. The control module 13 receives the first inspection signal 135A and accordingly drives the lifting unit 101 to move in the first direction, such that the lighting image capturing module 16 moves closer to the inspected object 3. The control module 13 controls the rotational shift unit 100 to drive the light emission element 100A to project the first spot light on the inspected object 3 through the opening 110. The control module 13 also controls the rotational shift unit 100 to move in the step manner towards the second or the third direction so as to carry the bearing module 11 to move accordingly. The control module 13 also controls the lighting image capturing module 16 to capture a plurality of images of the first region 30A and to generate a plurality of the first inspection images 160.

For example, the mask inspection device 1 of the present invention further includes the lighting image capturing module 16, which can have an auto-focus function. The lighting image capturing module 16 is disposed on the lifting unit 101 that is suspended on the surface of the device main body 10. In order to perform inspection on a lower surface of the inspected object 3, the operator inputs the first inspection signal 135A to the control module 13. According to the first inspection signal 135A, the control module 13 controls the lifting unit 101 to move in the first direction, such as the up/down direction or z-axis direction, such that the lighting image capturing module 16 moves closer to the inspected object 3. After that, the control module 13 controls the rotational shift unit 100 to drive the light emission element 100A so as to generate the first spot light, which is projected on the inspected object 3 through the opening 110. Also, the control module 13 controls the rotational shift unit 100 to step towards the second direction, such as forward/backward direction or y-axis direction, such that the lighting image capturing module 16 can capture an image of each first region 30A of entire lower surface of the inspected object 3 and generate a plurality of the first inspection images 160.

As a result, clear images of the first regions 30A of the lower surface of the inspected object 3 can be acquired by the operator to determine whether if there is any anomaly on the lower surface of the inspected object 3. In this way, the accuracy of the mask inspection can be improved.

Moreover, the control module 13 can receive the second inspection signal 135B and accordingly drive the lighting image capturing module 16 to project the second spot light on the inspected object 3. The control module 13 can also control the rotational shift unit 100 to step in the second or the third direction, and therefore to carry the bearing module 11 to move accordingly. The control module 13 also controls the lighting image capturing module 16 to capture a plurality of images of the second region 30B to generate a plurality of the second inspection images 161.

Therefore, the mask inspection device 1 of the present invention can further inspect the upper surface of the inspected object 3 to check whether if there is anomaly on it. When the operator inputs and sends the second inspection signal 135B to the control module 13, the control module 13 drives the lighting image capturing module 16 accordingly to project the second spot light on the inspected object 3 and controls the rotational shift unit 100 to step in the second direction, such as forward/backward or y-axis direction, or in the third direction, such as left/right or x-axis direction so as to carry the bearing module 11 to move accordingly. The control module 13 then controls the lighting image capturing module 16 to capture images of the second regions 30B of the entire upper surface of the inspected object 3 and accordingly to generate a plurality of the second inspection images 161.

As a result, clear images of the second regions 30B of the upper surface of the inspected object 3 can be acquired by the operator to determine whether if there is any anomaly on the upper surface of the inspected object 3. In this way, the accuracy of the mask inspection can be improved.

Preferably, the mask inspection device 1 can further include a distance measuring module 15, which is electrically connected to the control module 13 and disposed on the lifting unit 101. The control module 13 receives a measuring signal 134 and accordingly controls the distance measuring module 15 to project at least one distance measuring light on the inspected object 3. The distance measuring module 15 receives the distance measuring light reflected from the inspected object 3 to generate an inspection distance signal 150. The control module 13 receives the first inspection signal 135A and the inspection distance signal 150 and accordingly drives the lifting unit 101 to move in the first direction, such that the lighting image capturing module 16 is at a predetermined working distance spaced apart from the inspected object 3. The control module 13 controls the rotational shift unit 100 to drive the light emission element 100A to project the first spot light on the inspected object 3 through the opening 110, and controls the rotational shift unit 100 to carry the bearing module 11 to move. The control module 13 controls the lighting image capturing module 16 to capture images of the plurality of first regions 30A of the inspected object 3 for generating the first inspection images 160.

Therefore, the mask inspection device 1 of the present invention further includes the distance measuring module 15 which is electrically connected to the control module 13 and disposed on the lifting unit 101. In order to inspect the surface of the inspected object 3, an operator can first input and send the measuring signal 134 to the control module 13. The control module 13 therefore drives the distance measuring module 15 to project at least one distance measuring light on the inspected object 15, and at least one distance measuring light reflected by the inspected object 3 is received by the distance measuring module 15 to generate the inspection distance signal 150. The control module 13 can control the distance measuring module 15 to project the distance measuring light on various regions of the inspected object 3 to check if the inspected object 3 is horizontal or tilted. The control module 13 then receives the mask inspection signal 135 and the inspection distance signal 150 and accordingly to drive the lifting unit 101 to move in the first direction, such as up/down or z-axis direction, such that the lighting image capturing module 16 is at the predetermined working distance spaced apart from the inspected object 3. The predetermined working distance can be, but not limited to, in a range of 3 cm to 5 cm based on the thickness of the substrate of the inspected object 3. The control module 13 then controls the rotational shift unit 100 to step towards the second or the third direction to carry the inspected object 3 on the bearing module 11 to move, and controls the lighting image capturing module 16 to capture the image of each first region 30A of the inspected object 3, so as to generate a plurality of the first inspection images 160. It should be noted that, in comparison with the previous embodiment, the inspection distance signal 150 generated by the distance measuring module 15 in this embodiment can be used to adjust the focus of the lighting image capturing module 16.

Furthermore, the mask inspection device 1 can preferably further include the first lighting module 14, one end of which is movably connected to the device main body 10 and the other end of which is disposed with a condenser unit 140. The control module 13 receives the third inspection signal 135C and accordingly drives the lifting unit 101 to move in the first direction, such that the lighting image capturing module 16 moves closer to the inspected object 3. The control module 13 also controls the first lighting module 14 to move towards the bearing module 11, such that the condenser unit 140 moves to the position between the rotational shift unit 100 and bearing module 11 and correspondingly facing the lighting image capturing module 16. The control module 13 also controls the rotational shift unit 100 to carry the bearing module 11 to move and controls the condenser unit 140 to project a focused light through the opening 110 on one of a plurality of through holes 33 of the inspected object 3, such that the lighting image capturing module 16 captures and generates the images 162 of the plurality of through holes 33.

For example, the mask inspection device 1 of the present invention further includes the first lighting module 14, one end of which is movably connected to the same surface of the device main body 10 and the other end of which is disposed with a condenser unit 140. While receiving the third inspection signal 135C, the control module 13 accordingly drives the lifting unit 101 to move towards the first direction, such as up/down or z-axis direction, such that the lighting image capturing module 16 moves closer to and spaced apart from the inspected object 3 by the predetermined working distance. Meanwhile, the first capturing module 13 also controls the first lighting module 14 to move towards the bearing module 11, such that the condenser unit 140 moves to the position between the rotational shift unit 100 and bearing module 11, that is, under the bearing module 11. The condenser unit 140 coaxially corresponds in position to the lighting image capturing module 16.

The control module 13 then controls the rotational shift unit 100 to step towards the second or the third direction, such that the inspected object 3 on the bearing module 11 is carried to move. The control module also controls the condenser unit 140 to project focused light on the mask region 30 of the inspected object 3 through the opening 110, such that the lighting image capturing module 16 can sequentially capture and generate the images 162 of through holes 33 of the inspected object 3.

Figure 8:
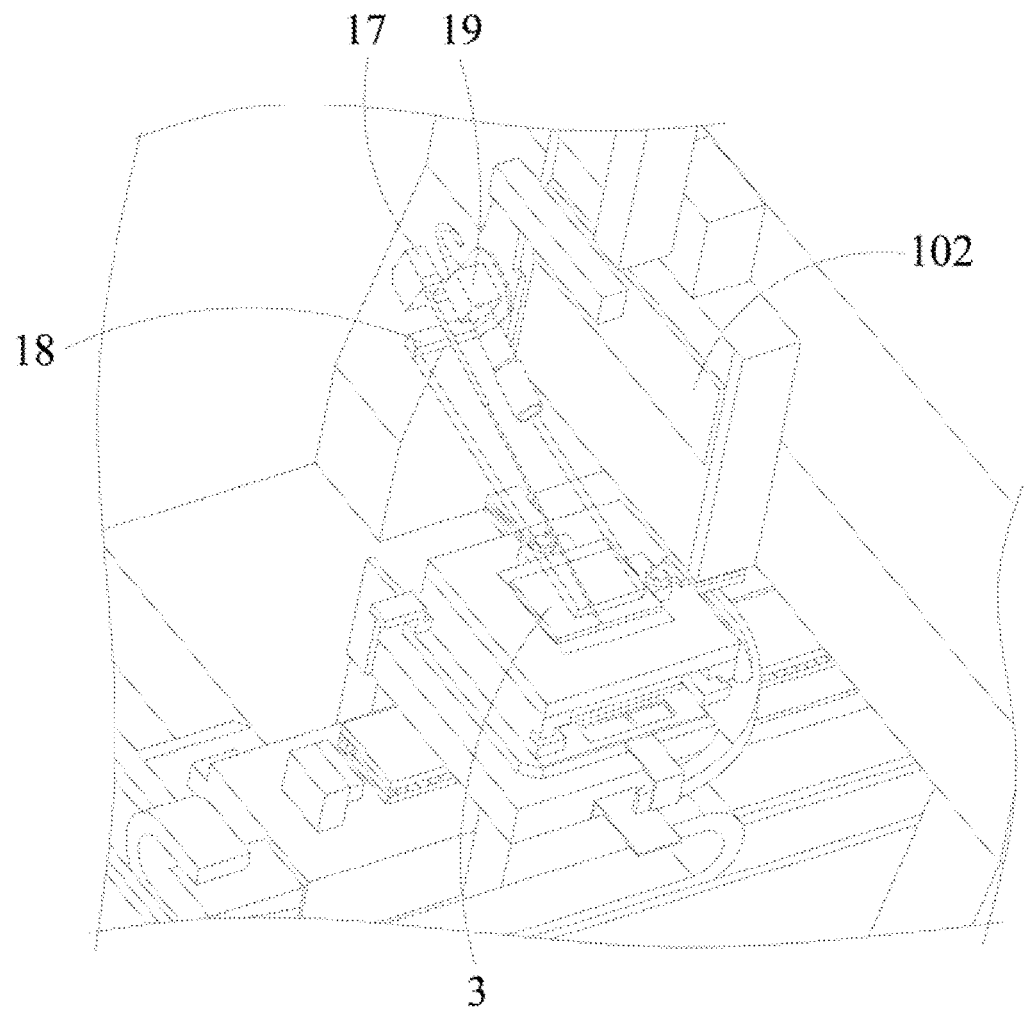
FIG. 8 is a first structural diagram showing a third embodiment of the mask inspection device of the present invention.
Figure 9:
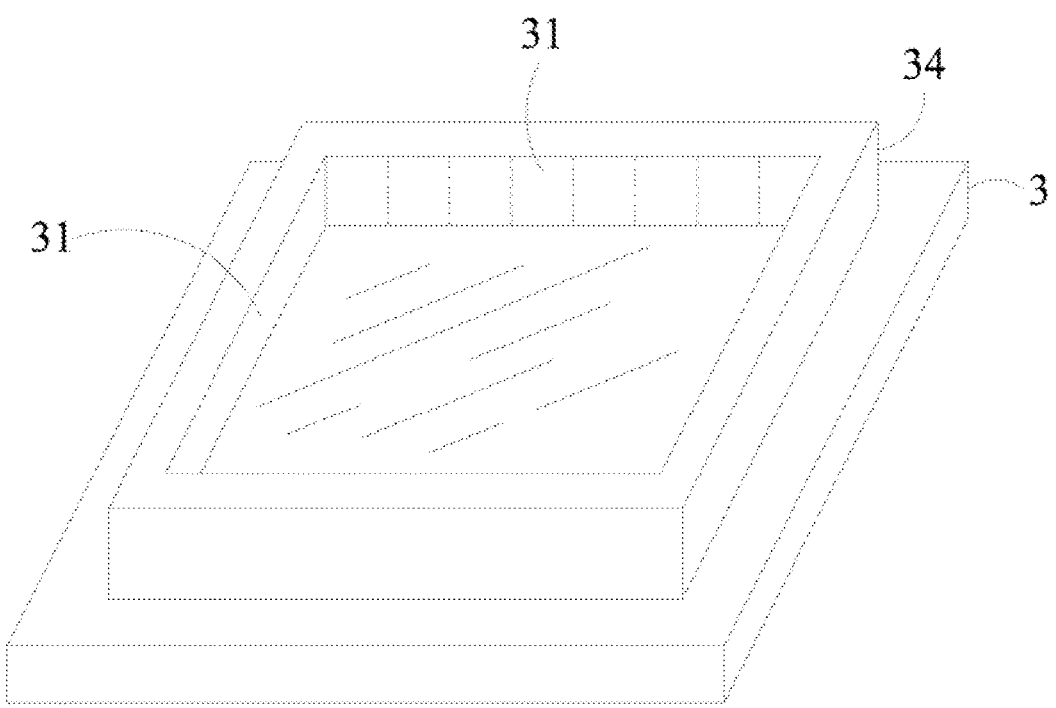
FIG. 9 is a second structural diagram showing the third embodiment of the mask inspection device of the present invention.

Referring to FIGS. 8-10, these are respectively the first schematic diagram, the second schematic diagram and the block diagram showing the third embodiment of the mask inspection device of the present invention. Also refer to FIGS. 1-7. As shown in the figures, the same elements act similarly as those in the first embodiment, so their descriptions are therefore omitted. It should be noted that, in this embodiment, a supporting unit 102 is disposed on the surface of the device main body 10, and the mask inspection device 1 further includes the second image capturing module 19, the first measuring module 17, and the second lighting module 18. The second image capturing module 19, which captures images of the inspected object 3, is disposed on the supporting unit 102. The first measuring module 17 is disposed on one side of the second image capturing module 19. The second lighting module 18 is disposed on the other side of the second image capturing module 19. The control module 13 receives a sidewall inspection signal 136 and accordingly controls the rotational shift unit 100 to carry the bearing module 11 to the image capturing region of the second image capturing module 19. The control module 13 also controls the rotational shift unit 100 to sequentially rotate the bearing module 11 and controls the first measuring module 17 to sequentially project the first measuring light on a plurality of inner wall surface 31 of the frame 34 on one surface of the inspected object 3. The first measuring module 17 receives the first measuring light reflected by the plurality of inner wall surfaces 31 to respectively generate the first distance inspection signals 170. Respectively based on the first distance inspection signals 170 corresponding to the inner wall surfaces 31, the control module 13 drives the rotational shift unit 100 to carry the bearing module 11 to move in the second or the third direction, so as to adjust the distance between each inner wall surface 31 and the second image capturing module 19 to the predetermined image capturing distance. The control module 13 also controls the second lighting module 18 to project the second spot light on each of the inner wall surfaces 31 and controls the second image capturing module 19 to sequentially capture the images of the inner wall surfaces, and generate a plurality of inner wall inspection images 190.

Specifically, the mask inspection device 1 of the present invention can further inspect the inner wall surface 31 of the inspected object 3, such as the inner wall surface 31 of the frame 34 of the inspected object 3. The mask inspection device 1 further includes the second image capturing module 19, the first measuring module 17, and the second lighting module 18. The second image capturing module 19 is disposed on the supporting unit 102, which is disposed on the surface of the device main body 10, and is utilized to capture the image of the inner wall surface 31 of the frame 34 of the inspected object 3. The first measuring module 17 is disposed on one side of the second image capturing module 19, and the second lighting module 18 is disposed on the other side of the second image capturing module 19. While the mask inspection device 1 performs the inspection operation on each inner wall surface 31 of the frame 34, the control module 13 receives the sidewall inspection signal 136 and controls to sequentially perform inspection operation on each inner wall surface 31 one by one, that is, the frame 34 will not be rotated for inspection of another inner wall surface 31 until the inspection for one of the inner wall surfaces 31 is completed. Therefore, the control module 13 firstly controls the rotational shift unit 100 to carry the bearing module 11 to move to the image capturing region of the second image capturing module 19. The control module 13 then controls the rotational shift unit 100 to sequentially rotate the bearing module 11 and also controls the first measuring module 17 to sequentially and respectively project the first measuring light on the plurality of inner wall surfaces 31 of the frame 34 of the inspected object 3. The first measuring module 17 receives the first measuring light reflected from each of the inner wall surfaces 31, so as to respectively generate the first distance inspection signals 170. The control module 13 then adjusts the distance between the inner wall surface 31 and the second image capturing module 19 to the predetermined image capturing distance, which is the focus distance of the second image capturing module 19, based on the first distance inspection signals 170. The control module 13 also controls the second image capturing module 19 to project the second spot light on the inner wall surface 31 of the inspected object 3 and controls the second image capturing module 19 to sequentially capture the images of the inner wall surfaces 31. After the inspection for the inner wall surfaces 31 are completed, a plurality of the first distance inspection signals 170 are generated, and each of these signals represents the distance between each region of the whole inner wall surface 31 and the first measuring module 17, and also represents the distance between each of the inner wall surfaces 31 and the second image capturing module 19. In this way, before the second image capturing module 19 captures the image of each of the inner wall surfaces 31, the control module 13 adjusts the predetermined image capturing distance between the second image capturing module 19 and the inner wall surface 31 based on the first distance inspection signal 170, such that the second image capturing module 19 can capture the clear image of the inner wall surface 31. The rotational shift unit 100 is driven in a step manner to carry the bearing module 11 to move in the second or the third direction, and the second image capturing module 19 is controlled to capture images of the inner wall region. As a result, the plurality of inner wall inspection images 190 can be generated for an operator to inspect if there is anomaly on the inner wall surface 31 of the inspected object 3.

Figure 11:
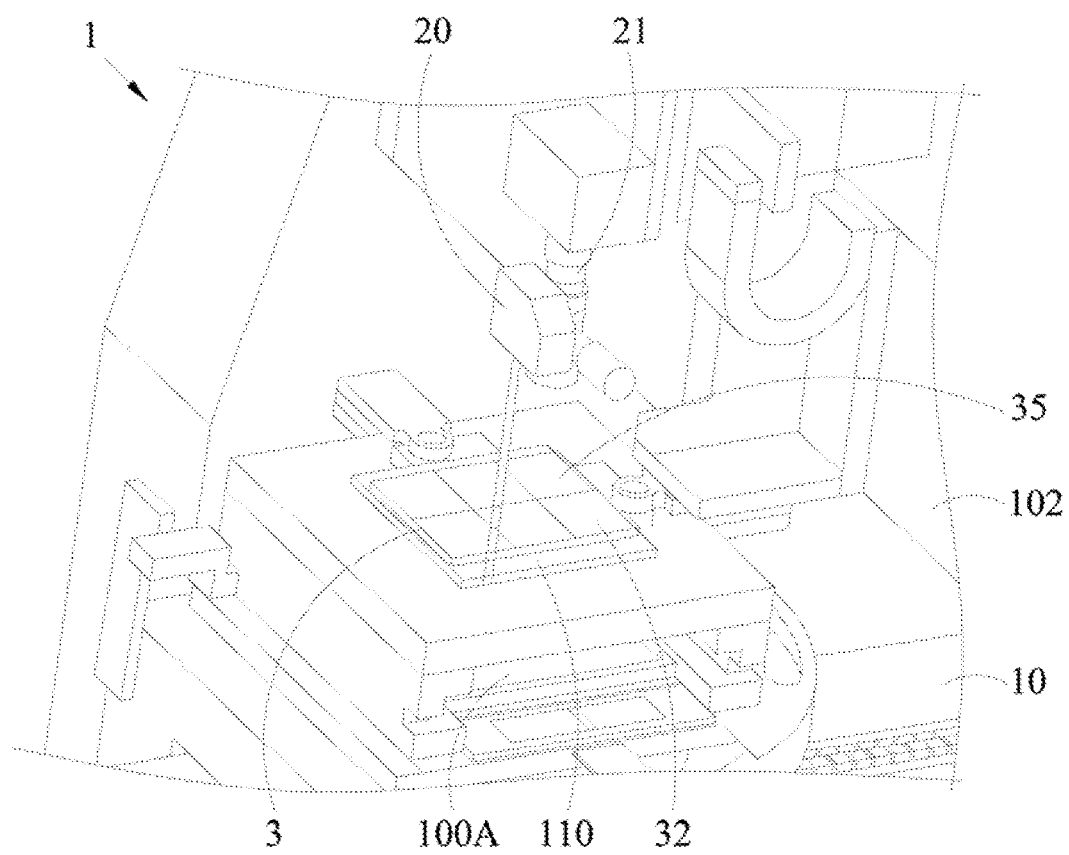
FIG. 11 is a structural diagram showing a fourth embodiment of the mask inspection device of the present invention.
Figure 12:
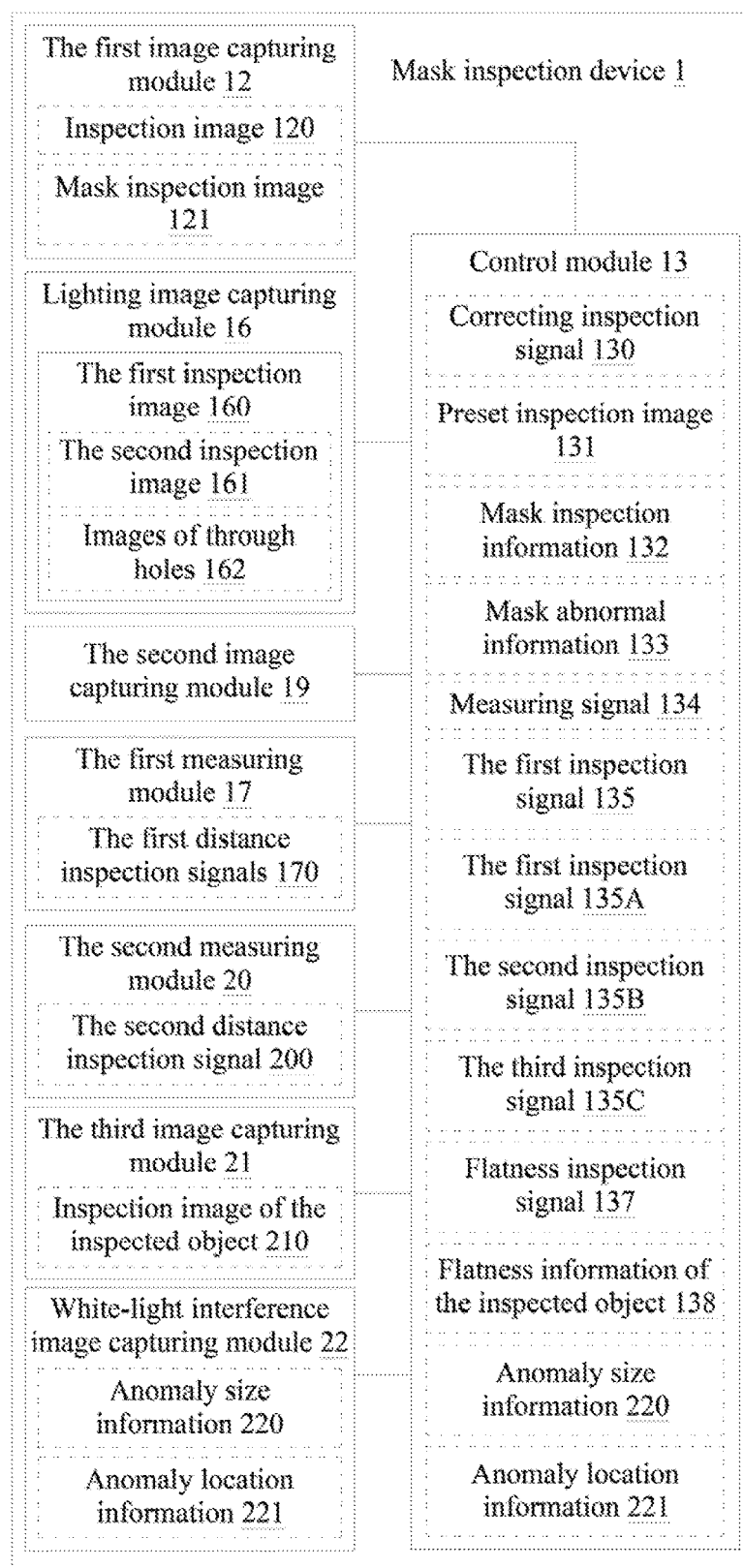
FIG. 12 is a block diagram showing the fourth embodiment of the mask inspection device of the present invention.

Referring to FIGS. 11 and 12, these are respectively the schematic diagram and the block diagram showing the fourth embodiment of the mask inspection device of the present invention. Also refer to FIGS. 1-10. As shown in the figures, the same elements act similarly as those in the first embodiment, so the descriptions are omitted. It should be noted that, in this embodiment, the supporting unit 102 is disposed on the surface of the device main body, and the mask inspection device 102 further includes a third image capturing module 21 and a second measuring module 20. The third image capturing module 21 is disposed on the supporting unit 102 to capture images of the inspected object 3. The second measuring module 20 is disposed on one side of the third image capturing module 21. The control module 13 receives the flatness inspection signal 137 and accordingly controls the rotational shift unit 100 to carry the bearing module 11 to move to the image capturing region of the third image capturing module 21. The control module 13 also controls the second measuring module 20 to sequentially project the second measuring light respectively on a plurality of surface regions 32 of the film body 35 of the inspected object 3 and to receive the second measuring light reflected from the plurality of surface regions 32, so as to generate the second distance inspection signal 200. The control module 13 controls the light emission element 100A to project the first spot light on the inspected object 3 through the opening 110 and sequentially controls the supporting unit 102 to move based on the plurality of the second distance inspection signals 200, so as to adjust the distance between the third image capturing module 21 and each surface region 32 to the predetermined image capturing distance. The control module 13 also controls the third image capturing module 21 to respectively capture image of each surface region 32 to generate a plurality of inspection images of the inspected object 210. The control module 13 generates the flatness information of the inspected object 138 based on the plurality of the second distance inspection signal 201.

For example, the mask inspection device 1 of the present invention can further inspect the flatness of the inspected object 3, such as the flatness of the thin film on the frame of the inspected object 3. Therefore, the mask inspection device 1 of the present invention can further include the third image capturing module 21 and the second measuring module 20. The third image capturing module 21 is disposed on the supporting unit 102, which is disposed on the surface of the device main body 10, and is utilized to capture images of the film body 35 of the inspected object 3. The film body 35 can be a dust-proof film being disposed on the frame 34. The second measuring module 20 is disposed on one side of the third image capturing module 21. While inspecting the flatness of the film body 35 of the inspected object 3, the mask inspection device 1 can also inspect whether there is anomaly on the surface of the film body 35. During the inspection, the control module 13 receives the flatness inspection signal 137 and accordingly controls the rotational shift unit 100 to carry the bearing module 11 to move to the image capturing region of the third image capturing module 21. Next, the control module 13 controls the second measuring module 20 to sequentially project the second measuring light on the plurality of surface regions 32 of the film body 35 of the inspected object 3 and receive the second measuring light reflected from each surface region 32 to generate a plurality of second distance inspection signals 200. In this way, the expansion level of the film body 35 can be acquired, and the working distance between the third image capturing module 21 and each surface region 32 can be adjusted. Then, the control module 13 controls the light emission element 100A to project the first spot light on the inspected object 3 through the opening 100A, and sequentially controls the supporting unit 102 to move based on the plurality of second distance inspection signal 200, so as to adjust the distance between the third image capturing module 21 and each surface region 32 to the predetermined image capturing distance. At the predetermined image capturing distance, the third image capturing module 21 can capture clear images of the surface regions 32. The control module 13 also controls the third image capturing module 21 to capture the image of each surface region 32 and generate the plurality of inspection images of the inspected object 210. The control module 13 finally translates the second distance inspection signal 201 into the flatness information of the inspected object 138 for the operator to recognize whether if the film body 35 is flat or uneven.

Furthermore, the mask inspection device 1 preferably includes a white-light interference image capturing module 22, which is electrically connected to the control module 13. The white-light interference image capturing module 22 receives the plurality of inspection images 190 of the inspected object and generates anomaly size information 220 and anomaly location information 221 by using a white light contrast interference manner. In this way, the mask inspection device 1 of the present invention can further include a white-light interference image capturing module 22, which receives the plurality of inspection images 190 of the inspected object and acquires the anomaly size information 220 (such as the size of an anomaly) of each anomaly and the anomalies location information 221, such as the coordinate information of anomalies on the inspected object 3. Therefore, according to the information 220 and 221, the operator can acquire the exact location of anomalies on the film body 35 for removing the anomalies. Meanwhile, through tomographic method, the white-light interference image capturing module 22 can also acquire the information about whether the anomaly is on the upper or lower surface of the film body 35.

In the previous description of the mask inspection device of the present invention, although the mask inspection method of the present invention has already been mentioned, the flow chart of the method will be illustrated hereinafter for the purpose of clarification.

Referring to FIG. 13, it is a first flow chart representing the mask inspection method of the present invention. Also refer to FIGS. 1 and 2. As shown in the figures, the mask inspection method of the present invention includes the steps as follows:

Step S40: after receiving the correcting inspection signal, the control module accordingly controls the first image capturing module to capture the image of the inspected object and accordingly to generate the inspection image;

Step S41: after receiving the inspection image, when the control module determines that the inspection image does not match the predetermined correction image, the control module controls the rotational shift unit to rotate horizontally to adjust the horizontal position and rotating angle of the bearing module, such that the horizontal position of the inspected object is therefore adjusted. When the control module determines that the inspection image matches the predetermined correction image, the control module controls the light emission element to project light on the inspected object through the opening, and also controls the first image capturing module to capture the image of the mask region of the inspected object, and therefore to generate the mask inspection image; and Step S42: after receiving and reading the two-dimensional image of the mask inspection image, the control module acquires the mask inspection information. The control module also inspects the abnormal image in the mask inspection image and accordingly generates the mask abnormal information.

Referring to FIGS. 14 and 15, these figures are respectively second and third flow charts representing the mask inspection method of the present invention. Also refer to FIGS. 1-7. As shown in the figures, the mask inspection method of the present invention preferably further includes the steps as follows:

Step 43: after receiving the first inspection signal, the control module accordingly drives the lifting unit to move in the first direction, such that the lighting image capturing module moves closer to the inspected object.

Step S44: the control module controls the rotational shift unit to drive the light emission element to project the first spot light on the inspected object through the opening and controls the rotational shift unit to move in the second or the third direction in the step manner, so as to drive movement of the bearing module; and Step S45: the control module controls the lighting image capturing module to capture the images of the plurality of the first regions of the inspected object, so as to generate the plurality of the first inspection images.

Furthermore, the mask inspection method preferably includes the steps as follows:

Step S46: after receiving the second inspection signal, the control module accordingly drives the lighting image capturing module to project the second spot light on the inspected object and controls the rotational shift unit to move in the second or the third direction in the step manner, so as to carry the bearing module to move; and Step S47: the control module controls the lighting image capturing module to capture images of the plurality of second regions of the inspected object, so as to generate the plurality of the second inspection images.

Furthermore, the mask inspection method preferably includes the steps as follows:

Step S48: after receiving the third inspection signal, the control module accordingly drives the lifting unit to move in the first direction, such that the lighting image capturing module moves closer to the inspected object;

Step S49: the control module controls the first lighting module to move towards the bearing module, such that the condenser unit moves to the position between the rotational shift unit and the bearing module and correspondingly facing the lighting image capturing module;

Step S50: the control module controls the rotational shift unit to carry the bearing module to move, and controls the condenser unit to project the focused light on one of the plurality of openings of the inspected object through the opening; and Step S51: the control module controls the lighting image capturing module to sequentially capture the images of the plurality of openings and generates the plurality of opening images.

Furthermore, the mask inspection method preferably includes the steps as follows:

Step S450: after receiving the measuring signal, the control module accordingly controls the distance measuring module to project at least one distance measuring light on the inspected object;

Step S451: the distance measuring module receives at least one distance measuring light reflected from the inspected object to generate the inspection distance signal;

Step S452: after receiving the first inspection signal and the inspection distance signal, the control module accordingly drives the lifting unit to move in the first direction, such that the lighting image capturing module is at the predetermined working distance away from the inspected object;

Step S453: the control module controls the rotational shift unit to drive the light emission element to project the first spot light on the inspected object through the opening, and controls the rotational shift unit to carry the bearing module to move; and Step S454: the control module controls the lighting image capturing module to capture the images of the plurality of first regions of the inspected object, so as to generate the plurality of the first inspection images.

Referring to FIG. 16, the figure is the fourth flow chart of the mask inspection method of the present invention. Also refer to FIGS. 1-10. As shown in the figures, the mask inspection method of the present invention preferably further includes the steps as follows:

Step S52: after receiving the sidewall inspection signal, the control module accordingly controls the rotational shift unit to carry the bearing module to move to the image capturing region of the second image capturing module.

Step S53: the control module controls the first measuring module to sequentially and respectively project the plurality of first measuring lights on the plurality of inner wall surfaces of the frame on one surface of the inspected object, and to receive the first measuring light reflected from each of inner wall surfaces to respectively generate the first distance inspection signals; and Step S54: respectively based on the plurality of first distance inspection signals of inner wall surfaces, the control module controls the rotational shift unit to sequentially carry the bearing module to move in the second or the third direction or to rotate horizontally, so as to adjust the distance between each inner wall surface and the second image capturing module to the predetermined image capturing distance. The control module also controls the second lighting module to project the third spot light on each inner wall surface and controls the second image capturing module to sequentially capture the image of each of inner wall surfaces, so as to generate the plurality of inner wall inspection images.

Referring to FIG. 17, the figure is the fifth flow chart of the mask inspection method of the present invention. Also refer to FIGS. 1-12. As shown in the figures, the mask inspection method of the present invention preferably further includes the steps as follows:

Step S55: after receiving the flatness inspection signal, the control module accordingly controls the rotational shift unit to carry the bearing module to move to the image capturing region of the third image capturing module;

Step S56: the control module controls the second measuring module to sequentially and respectively project the second measuring light on the plurality of surface regions of the film body of the inspected object and, and then receive the second measuring light reflected from the inspected object, so as to generate the plurality of the second distance inspection signals. The control module also controls the light emission element to project first spot light on the inspected object through the opening and controls the third image capturing module to capture images of the inspected object so as to generate the plurality of inspection images of the inspected object;

Step S57: the control module controls the light emission element to project the first spot light on the inspected object through the opening and sequentially controls the supporting unit to move according to the plurality of second distance inspection signals, so as to adjust the distance between the third image capturing module and each surface region to the predetermined image capturing distance;

Step S58: the control module controls the third image capturing module to respectively capture the image of each of the surface regions, so as to generate the plurality of inspection images of the inspected object; and Step S59: the control module generates the flatness information of the inspected object based on the plurality of the second distance inspection signals.

Furthermore, the mask inspection method preferably includes the steps as follows:

Step S60: the white-light interference image capturing module receives the plurality of inspection images of the inspected object and generates the anomaly size information and the anomaly location information by using the white light contrast interference manner.

The description above is only for the purpose of illustration but not restriction. Without departing from the spirit of the present application, any equivalent modification or alteration should be considered as falling within the protection scope of the appended claims.

What is claimed is:

1. A mask inspection device, comprising:
a device main body, a surface of which is movably disposed with a rotational shift unit, and a surface of the rotational shift unit is disposed with a light emission element;
a bearing module suspended on the surface of the rotational shift unit, wherein an inspected object is movably carried on other surface of the bearing module opposing to the surface of the bearing module facing the rotational shift unit, and a main body of the bearing module has an opening;
a first image capturing module suspended on the surface of the device main body; and
a control module electrically connected with the rotational shift unit and the first image capturing module, wherein the control module receives a correcting inspection signal and accordingly controls the first image capturing module to capture the image of the inspected object so as to generate an inspection image;
wherein after receiving the inspection image, when the control module determines that the inspection image does not match a predetermined correction image, the control module controls the rotational shift unit to rotate horizontally so as to adjust the horizontal position and a rotational angle of the bearing module, such that the horizontal position of the inspected object is adjusted; wherein when control module determines that the inspection image matches the predetermined correction image, the control module controls the light emission element to project a first spot light on the inspected object and controls the first image capturing module to capture the image of a mask region of the inspected object so as to generate a mask inspection image, and the control module receives and reads a two-dimensional image of the mask inspection image to acquire mask inspection information and inspects the abnormal image in the mask inspection image to generate mask abnormal information.

2. The mask inspection device of claim 1, wherein the surface of the device main body is disposed with a lifting unit, and the mask inspection device further comprises:
a lighting image capturing module disposed on the lifting unit, wherein the control module receives a first inspection signal and accordingly drives the lifting unit to move in a first direction, such that the lighting image capturing module is closer to the inspected object, and the control module controls the rotational shift unit to drive the light emission element to project the first spot light on the inspected object through the opening and controls the rotational shift unit to move in a second direction or in a third direction in a step manner, so as to carry the bearing module to move; wherein the control module also controls the lighting image capturing module to capture images of a plurality of first regions of the inspected object, so as to generate a plurality of first inspection images.

3. The mask inspection device of claim 2, wherein the control module receives a second inspection signal and accordingly drives the lighting image capturing module to project a second spot light on the inspected object, and the control module controls the rotational shift unit to move in the second direction or the third direction in the step manner, to drive movement of the bearing module, and the control module controls the lighting image capturing module to capture images of a plurality of second regions of the inspected object, so as to generate a plurality of second inspection images.

4. The mask inspection device of claim 2, further comprising a distance measuring module electrically connected to the control module and disposed on the lifting unit, wherein the control module receives a measuring signal and accordingly controls the distance measuring module to project at least one distance measuring light on the inspected object, and the distance measuring module receives at least one distance measuring light reflected from the inspected object to generate an inspection distance signal, and the control module receives the first inspection signal and the inspection distance signal and accordingly drives the lifting unit to move in the first direction, such that the lighting image capturing module is spaced apart from the inspected object by a predetermined working distance, and the control module controls the rotational shift unit to drive the light emission element to project the first spot light on the inspected object through the opening and controls the rotational shift unit to carry the bearing module to move, and the control module controls the lighting image capturing module to capture the images of the plurality of the first regions of the inspected object, so as to generate the plurality of first inspection images.

5. The mask inspection device of claim 2, further comprising a first lighting module, an end of which is movably disposed on the device main body and the other end of which is disposed with a condenser unit, wherein the control module receives a third inspection signal and accordingly drives the lifting unit to move in the first direction so as to move the lighting image capturing module closer to the inspected object and controls the first lighting module to move towards the bearing module, such that the condenser unit moves to the position between the rotational shift unit and the bearing module and correspondingly facing the lighting image capturing module, and the control module controls the rotational shift unit to carry the bearing module to move and controls the condenser unit to project a focused light on one of a plurality of through holes of the inspected object through the opening, such that the lighting image capturing module sequentially captures the images of the plurality of through holes and generates images of the plurality of through holes.

6. The mask inspection device of claim 1, wherein the surface of the device main body is disposed with a supporting unit, and the mask inspection device further comprises:
a second image capturing module disposed on the supporting unit to capture the image of the inspected object;
a first measuring module disposed on one side of the second image capturing module; and
a second lighting module disposed on the other side of the second image capturing module;
wherein the control module receives a sidewall inspection signal and accordingly controls the rotational shift unit to carry the bearing module to move to the image capturing region of the second image capturing module, and the control module controls the rotational shift unit to sequentially rotate the bearing module and controls the first measuring module to sequentially project first measuring light on a plurality of inner wall surfaces of a frame on a surface of the inspected object, and the first measuring module receives the first measuring light reflected from each of the inner wall surfaces to generate a first distance inspection signal, and correspondingly based on the plurality of first distance inspection signals, the control module drives the rotational shift unit to carry the bearing module to move in a second direction or a third direction or to rotate horizontally so as to adjust the distance between each inner wall surface and the second image capturing module to a predetermined image capturing distance, and controls the second lighting module to project a third spot light on each inner wall surface and controls the second image capturing module to sequentially capture images of inner wall surfaces, so as to generate a plurality of inner wall inspection images.

7. The mask inspection device of claim 1, wherein the surface of the device main body is disposed with a supporting unit, and the mask inspection device further comprises:
a third image capturing module disposed on the supporting unit to capture the image of the inspected object; and
a second measuring module disposed on one side of the third image capturing module;
wherein the control module receives a flatness inspection signal and accordingly controls the rotational shift unit to carry the bearing module to move to the image capturing region of the third image capturing module, and the control module controls the second measuring module to sequentially project a second measuring light on each of a plurality of surface regions of a film body of the inspected object and to receive the second measuring light reflected from the plurality of surface regions so as to generate a plurality of second distance inspection signals, and the control module controls the light emission element to project the first spot light on the inspected object through the opening, and sequentially controls the supporting unit to move based on the plurality of second distance inspection signals so as to adjust the distance between the third image capturing module and each of the surface regions to a predetermined image capturing distance, and the control module respectively controls the third image capturing module to respectively capture the images of the surface regions to generate a plurality of inspection images of the inspected object, and the control module generates flatness information of the inspected object based on the plurality of the second distance inspection signals.

8. The mask inspection device of claim 7, further comprising a white-light interference image capturing module electrically connected to the control module, wherein the white-light interference image capturing module receives the plurality of inspection images of the inspected object to generate anomaly size information and anomaly location information by using a white light contrast interference manner.

9. A mask inspection method, comprising the steps of:
upon receipt of a correcting inspection signal, controlling a first image capturing module to capture the image of an inspected object and accordingly to generate an inspection image, by a control module;
upon receipt of the inspection image, when the control module determines that the inspection image does not match a predetermined correction image, controlling a rotational shift unit to rotate horizontally so as to adjust a horizontal position and a rotating angle of a bearing module and adjust the horizontal position of the inspected object; when the control module determines that the inspection image matches the predetermined correction image, controlling a light emission element to project light on the inspected object through an opening and controlling the first image capturing module to capture an image of a mask region of the inspected object and to generate a mask inspection image; and
after the control module receives and reads a two-dimensional image of the mask inspection image, using the control module to acquire mask inspection information, and inspect an abnormal image in the mask inspection image to generate mask abnormal information, by the control module.

10. The mask inspection method of claim 9, further comprising the steps of:
upon receipt of a first inspection signal, driving a lifting unit to move in a first direction, so as to move a lighting image capturing module closer to the inspected object;
controlling the rotational shift unit to drive the light emission element to project a first spot light on the inspected object through the opening and controlling the rotational shift unit to move in a second or a third direction in a step manner, so as to carry the bearing module to move; and
controlling the lighting image capturing module to capture the images of a plurality of first regions of the inspected object and to generate a plurality of first inspection images.

11. The mask inspection method of claim 10, further comprising the steps of:
upon receipt of a second inspection signal, driving the lighting image capturing module to project a second spot light on the inspected object, and controlling the rotational shift unit to move in the second or the third direction in the step manner, so as to carry the bearing module to move; and
controlling the lighting image capturing module to capture the images of a plurality of second regions of the inspected object, so as to generate a plurality of second inspection images.

12. The mask inspection method of claim 10, further comprising the steps of:
upon receipt of a measuring signal, controlling a distance measuring module to project at least one distance measuring light on the inspected object;
using the at least one distance measuring module to receive distance measuring light reflected from the inspected object, so as to generate an inspection distance signal;
upon receipt of the first inspection signal and the inspection distance signal, driving the lifting unit to move in the first direction, such that the lighting image capturing module is spaces apart from the inspected object by a predetermined working distance;
controlling the rotational shift unit, by the control module, to drive the light emission element to project the first spot light on the inspected object through the opening, and controlling the rotational shift unit to carry the bearing module to move; and
controlling the lighting image capturing module, by the control module, to capture the images of a plurality of first regions, so as to generate a plurality of first inspection images.

13. The mask inspection method of claim 10, further comprising the steps of:
upon receipt of a third inspection signal, driving the lifting unit to move in the first direction, so as to move the lighting image capturing module closer to the inspected object;
controlling a first lighting module, by the control module, to move towards the bearing module, so as to move a condenser unit to the position between the rotational shift unit and the bearing module and correspondingly facing the lighting image capturing module;
controlling the rotational shift unit, by the control module, to carry the bearing module to move, and controlling the condenser unit to project a focused light on one of a plurality of through holes of the inspected object through the opening; and
controlling the lighting image capturing module, by the control module, to sequentially capture the images of the plurality of through holes and to generate a plurality of opening images.

14. The mask inspection method of claim 9, further comprising the steps of:
upon receipt of a sidewall inspection signal, controlling the rotational shift unit to carry the bearing module to move to an image capturing region of a second image capturing module;
controlling the rotational shift unit, by the control module, to sequentially rotate the bearing module, and controlling a first measuring module to sequentially and respectively project a plurality of first measuring lights on a plurality of inner wall surfaces of a frame of the inspected object, and using the first measuring module to receive the first measuring light reflected from each of the inner wall surfaces to respectively generate a first distance inspection signal; and
respectively based on the plurality of first distance inspection signals of each inner wall surface, controlling the rotational shift unit, by the control module, to sequentially carry the bearing module to move in a second or a third direction or to rotate horizontally so as to adjust the distance between each inner wall surface and the second image capturing module to a predetermined image capturing distance, and controlling a second lighting module, by the control module, to project a third spot light on each of the inner wall surfaces, and controlling the second image capturing module to sequentially capture the image of each inner wall surface so as to generate a plurality of inner wall inspection images.

15. The mask inspection method of claim 14, further comprising the steps of:
upon receipt of a flatness inspection signal, controlling the rotational shift unit to carry the bearing module to move to an image capturing region of a third image capturing module;

controlling a second measuring module, by the control module, to sequentially and respectively project second measuring light on a plurality of surface regions of a film body of the inspected object and to receive the second measuring light reflected from the inspected object so as to generate a plurality of second distance inspection signals;

controlling the light emission element, by the control module, to project a first spot light on the inspected object through the opening, and sequentially controlling a supporting unit to move based on the plurality of second distance inspection signals, so as to adjust the distance between the third image capturing module and each of the surface regions to the predetermined image capturing distance; and controlling the third image capturing module, by the control module, to respectively capture the images of the surface regions so as to generate a plurality of inspection images of the inspected object; and generating flatness information of the inspected object based on the plurality of the second distance inspection signals.

16. The mask inspection method of claim 10, further comprising the steps of:

using a white-light interference image capturing module to receive a plurality of inspection images of the inspected object; and generating anomaly size information and anomaly location information by using a white light contrast interference manner.

* * * * *